(12) United States Patent
Zones et al.

(10) Patent No.: US 11,161,749 B1
(45) Date of Patent: Nov. 2, 2021

(54) MOLECULAR SIEVE SSZ-120, ITS SYNTHESIS AND USE

(71) Applicant: CHEVRON U.S.A. INC., San Ramon, CA (US)

(72) Inventors: Stacey Ian Zones, San Francisco, CA (US); Jesus Pascual, Berkeley, CA (US); Dan Xie, Richmond, CA (US); Cong-Yan Chen, Kensington, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 17/323,005

(22) Filed: May 18, 2021

Related U.S. Application Data

(60) Provisional application No. 63/028,642, filed on May 22, 2020.

(51) Int. Cl.
| | | |
|---|---|---|
| *C01B 39/06* | (2006.01) |
| *C01B 39/48* | (2006.01) |
| *B01J 29/70* | (2006.01) |
| *C01B 39/20* | (2006.01) |
| *C01B 39/02* | (2006.01) |

(52) U.S. Cl.
CPC ............... *C01B 39/06* (2013.01); *B01J 29/70* (2013.01); *C01B 39/026* (2013.01); *C01B 39/20* (2013.01); *C01B 39/48* (2013.01); *C01P 2002/72* (2013.01); *C01P 2006/12* (2013.01)

(58) Field of Classification Search
CPC ....... C01B 39/026; C01B 39/06; C01B 39/48; B01J 29/70; C01P 2002/72
See application file for complete search history.

(56) References Cited

U.S. PATENT DOCUMENTS

| | | | |
|---|---|---|---|
| 6,896,869 B2 | 5/2005 | Corma Canos et al. |
| 7,014,836 B2 | 3/2006 | Corma Canos et al. |
| 7,074,385 B2 | 7/2006 | Harbuzaru et al. |
| 8,101,154 B2 | 1/2012 | Lorgouilloux et al. |
| 8,124,038 B2 | 2/2012 | Lorgouilloux et al. |
| 8,361,436 B2 | 1/2013 | Lorgouilloux et al. |
| 8,372,376 B2 | 2/2013 | Caullet et al. |
| 8,372,377 B2 | 2/2013 | Lorgouilloux et al. |
| 8,444,952 B2 | 5/2013 | Dodin et al. |
| 10,155,666 B2 | 12/2018 | Zones |
| 10,384,951 B1 | 8/2019 | Zones et al. |
| 2021/0220807 A1* | 7/2021 | Zones ..................... B01J 37/10 |

OTHER PUBLICATIONS

T. Conradsson, M.S. Dadachov and X.D. Zou "Synthesis and structure of (Me3N)6[Ge32O64](H2O)4.5, a thermally stable novel zeotype with 3D interconnected 12-ring channels" Micropor. Mesopor. Mater. 2000, 41, 183-191.

(Continued)

*Primary Examiner* — David M Brunsman

(57) ABSTRACT

A small crystal size, high surface area aluminogermanosilicate molecular sieve material, designated SSZ-120, is provided. SSZ-120 can be synthesized using 3,3'-[2,6-naphthalenebis(methylene)]bis[1,2-dimethyl-1H-imidazolium] dications as a structure directing agent. SSZ-120 may be used in organic compound conversion reactions and/or sorptive processes.

14 Claims, 5 Drawing Sheets

(56) References Cited

OTHER PUBLICATIONS

Z. Liu, T. Ohsuna, O. Terasaki, M.A. Camblor, M-J. Diaz-Cabanas and K. Hiraga "The First Zeolite with Three-Dimensional Intersecting Straight-Channel System of 12-Membered Rings" J. Am. Chem. Soc. 2001, 123, 5370-5371.

M.A. Camblor, P.A. Barrett, M-J. Diaz-Cabanas, L.A. Villaescusa, M. Puche, T. Boix, E. Perez and H. Koller "High silica zeolites with three-dimensional systems of large pore channels" Micropor. Mesopor. Mater. 2001, 48, 11-22.

L. Tosheva, N. Mahe and V. Valtchev "One-pot template extraction and alumination of BEC-type zeolite" From Zeolites to Porous MOF Materials—the 40th Anniversary of the International Zeolite Conference, 2007, 616-621.

L. Shi, Y. Yuan, N. Zhang, S. Lin, T. Yu and J. Wang "Synthesis and characterization of BEC-zeotype germanosilicates and B-substituted zeolitic materials" J. Porous Mater. 2016, 23, 647-654.

* cited by examiner

MOLECULAR SIEVE SSZ-120, ITS SYNTHESIS AND USE

CROSS-REFERENCE TO RELATED APPLICATIONS

This application claims priority to and the benefit of U.S. Provisional Application Ser. No. 63/028,642, filed May 22, 2020.

FIELD

This disclosure relates to a small crystal size, high surface area aluminogermanosilicate molecular sieve designated SSZ-120, its synthesis, and its use in organic compound conversion reactions and sorption processes.

BACKGROUND

Molecular sieves are a commercially important class of materials that have distinct crystal structures with defined pore structures that are shown by distinct X-ray diffraction (XRD) patterns and have specific chemical compositions. The crystal structure defines cavities and pores that are characteristic of the specific type of molecular sieve.

According to the present disclosure, a small crystal size, high surface area aluminogermanosilicate molecular sieve, designated SSZ-120 and having a unique powder X-ray diffraction pattern, has been synthesized using 3,3'-[2,6-naphthalenebis(methylene)]bis[1,2-dimethyl-1H-imidazolium] dications as a structure directing agent.

SUMMARY

In a first aspect, there is provided an aluminogermanosilicate molecular sieve having, in its calcined form, a powder X-ray diffraction pattern including the peaks in the following table:

| 2-Theta [°] | d-Spacing [nm] | Relative Intensity [100 × I/Io] |
|---|---|---|
| 6.8 | 1.30 | W |
| 9.5 | 0.93 | W |
| 15.6 | 0.57 | M |
| 21.0 | 0.42 | W |
| 22.2 | 0.40 | VS |
| 25.9 | 0.34 | M |
| 26.9 | 0.33 | M. |

The calcined molecular sieve can have a total surface area (as determined by the t-plot method for nitrogen physisorption) of at least 500 m²/g and/or an external surface area (as determined by the t-plot method for nitrogen physisorption) of at least 100 m²/g.

In a second aspect, there is provided an aluminogermanosilicate molecular sieve having, in its as-synthesized form, a powder X-ray diffraction pattern including the peaks in the following table:

| 2-Theta [°] | d-Spacing [nm] | Relative Intensity [100 × I/Io] |
|---|---|---|
| 6.8 | 1.31 | W |
| 9.4 | 0.94 | W |
| 15.7 | 0.57 | M |
| 21.0 | 0.42 | M |
| 22.0 | 0.40 | VS |
| 25.9 | 0.34 | M |
| 26.9 | 0.33 | M |

In its as-synthesized and anhydrous form, the aluminogermanosilicate molecular sieve can have a chemical composition comprising the following molar relationship:

|  | Broadest | Secondary |
|---|---|---|
| $(SiO_2 + GeO_2)/Al_2O_3$ | ≥30 | ≥60 |
| $Q/(SiO_2 + GeO_2)$ | >0 to 0.1 | >0 to 0.1 | wherein Q comprises 3,3'-[2,6-naphthalenebis(methylene)]bis[1,2-dimethyl-1H-imidazolium] dications.

In a third aspect, there is provided a method of synthesizing an aluminogermanosilicate molecular sieve, the method comprising (1) providing a reaction mixture comprising: (a) a FAU framework type zeolite; (b) a source of germanium; (c) a structure directing agent (Q) comprising 3,3'-[2,6-naphthalenebis(methylene)]bis[1,2-dimethyl-1H-imidazolium] dications; (d) a source of fluoride ions; and (e) water; and (2) subjecting the reaction mixture to crystallization conditions sufficient to form crystals of the aluminogermanosilicate molecular sieve.

In a fourth aspect, there is provided a process of converting a feedstock comprising an organic compound to a conversion product which comprises contacting the feedstock at organic compound conversion conditions with a catalyst comprising an active form of the aluminogermanosilicate molecular sieve, described herein.

In a fifth aspect, there is provided an organic nitrogen compound comprising a dication having the following structure:

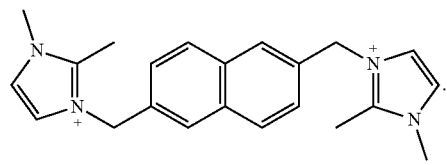

DETAILED DESCRIPTION

Definitions

Figure 1:
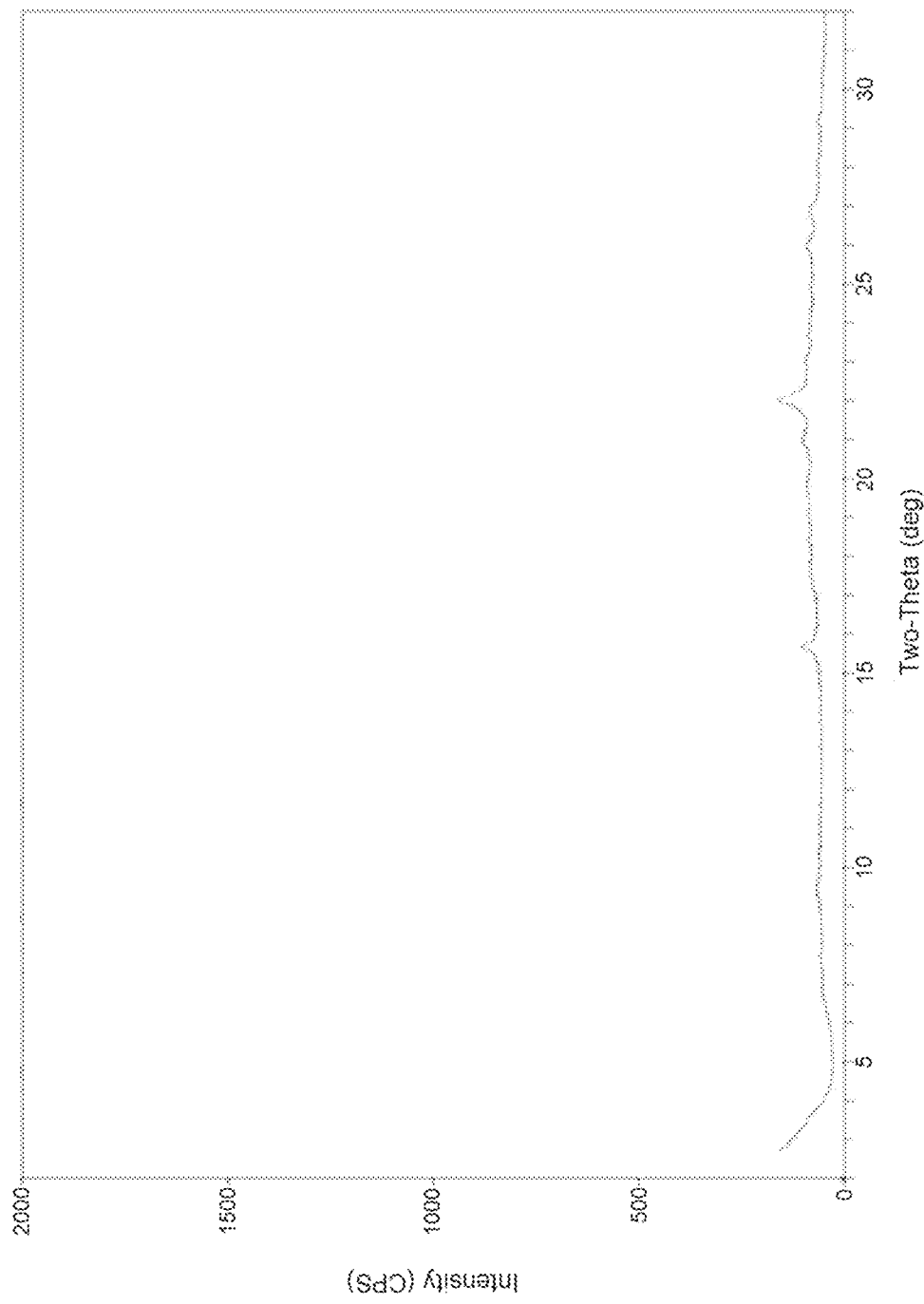
FIG. 1 shows the powder X-ray diffraction (XRD) pattern of the as-synthesized product of Example 2.
Figure 2A:
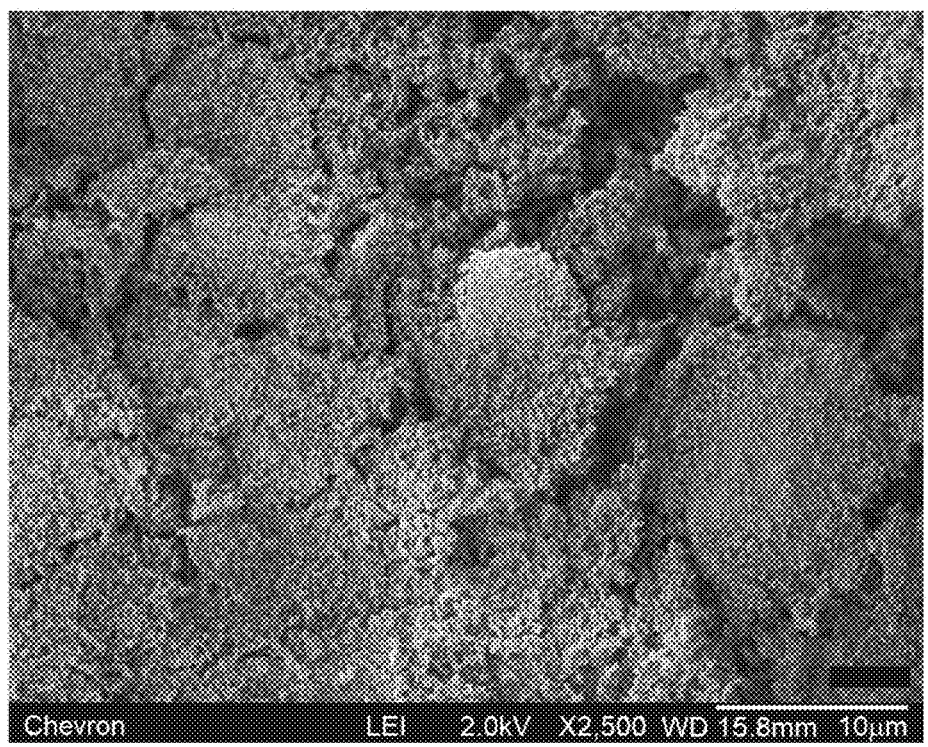
FIGS. 2(A)-2(D) show scanning electron micrograph (SEM) images of the as-synthesized product of Example 2 at different magnifications.
Figure 2B:
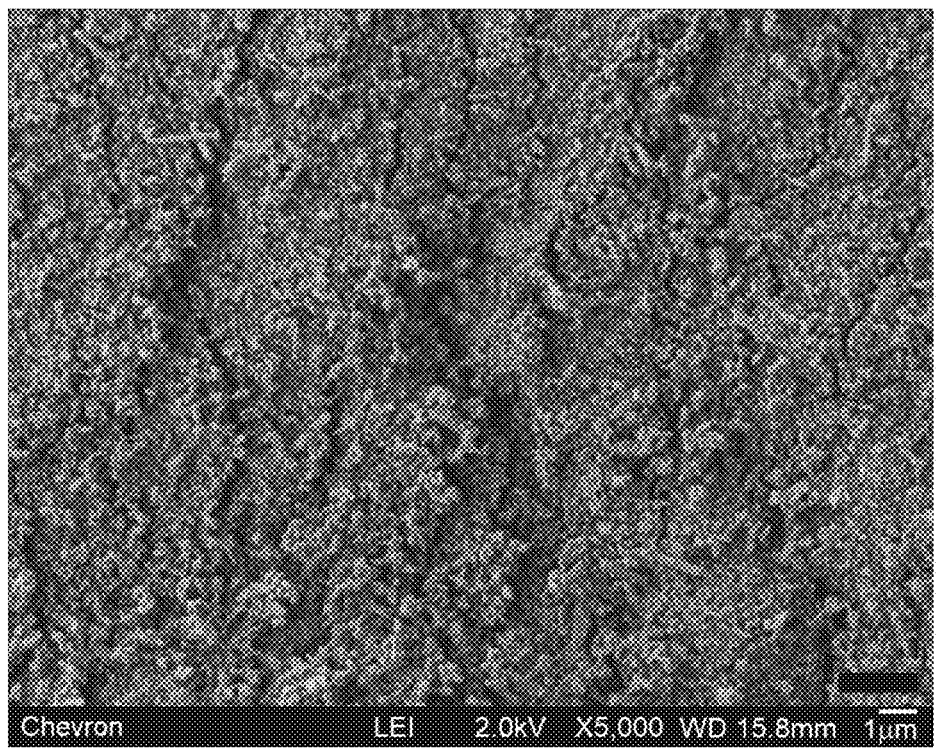
Figure 2C:
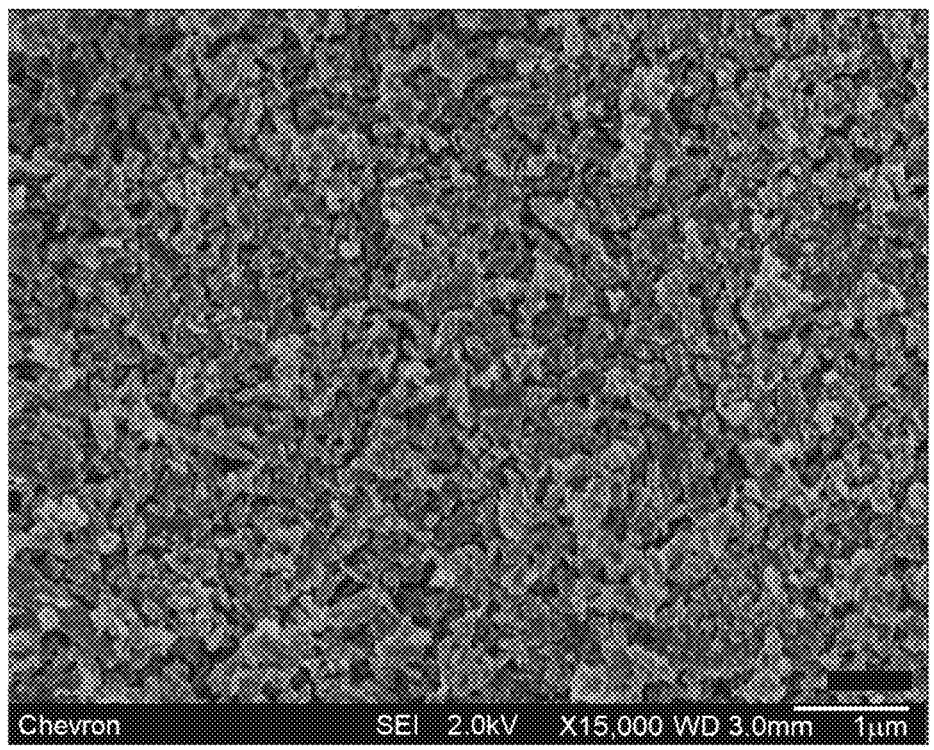
Figure 2D:
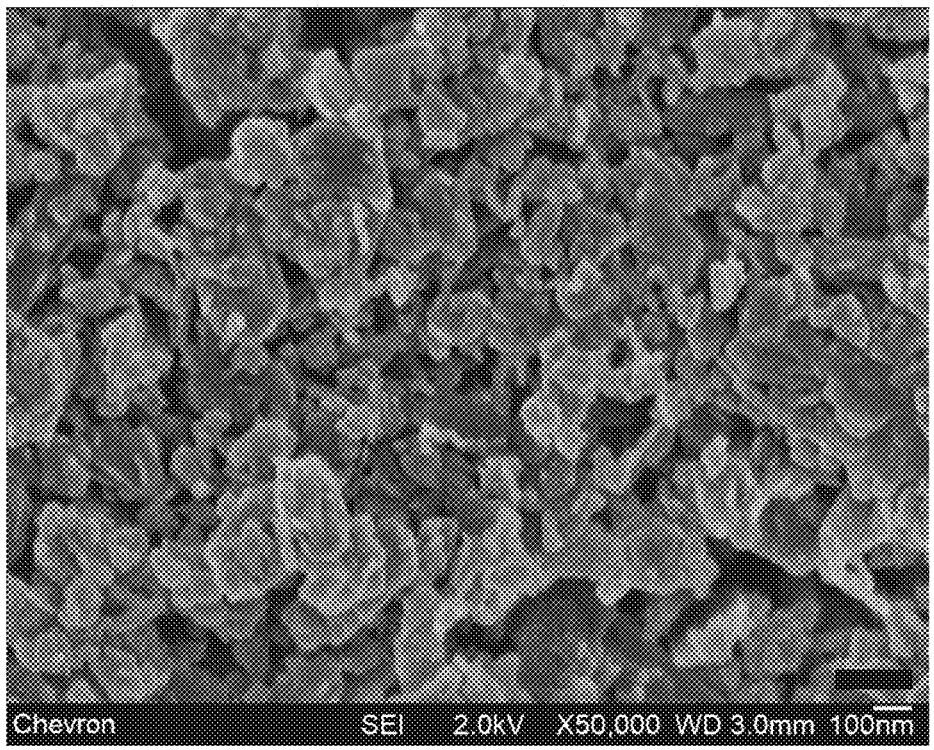

The term "framework type" has the meaning described in the "*Atlas of Zeolite Framework Types*", by Ch. Baerlocher and L. B. McCusker and D. H. Olsen (Sixth Revised Edition, Elsevier, 2007).

The term "zeolite" refers an aluminosilicate molecular sieve having a framework constructed of alumina and silica (i.e., repeating AlO4 and SiO4 tetrahedral units).

The term "aluminogermanosilicate" refers to a molecular sieve having a framework constructed of AlO4, GeO4 and SiO4 tetrahedral units. The alumingermanosilicate may contain only the named oxides, in which case, it may be described as a "pure aluminogermanosilicate" or it may contain other additional oxides as well.

The term "as-synthesized" is employed herein to refer to a molecular sieve in its form after crystallization, prior to removal of the structure directing agent.

The term "anhydrous" is employed herein to refer to a molecular sieve substantially devoid of both physically adsorbed and chemically adsorbed water.

The term "$SiO_2/Al_2O_3$ molar ratio" may be abbreviated as "SAR".

Synthesis of the Molecular Sieve

Aluminogermanosilicate molecular sieve SSZ-120 can be synthesized by: (1) providing a reaction mixture comprising (a) a FAU framework type zeolite; (b) a source of germanium; (c) a structure directing agent (Q) comprising 3,3'-[2,6-naphthalenebis(methylene)]bis[1,2-dimethyl-1H-imidazolium] dications; (d) a source of fluoride ions; and (e) water; and (2) subjecting the reaction mixture to crystallization conditions sufficient to form crystals of the aluminogermanosilicate molecular sieve.

The reaction mixture can have a composition, in terms of molar ratios, within the ranges set forth in Table 1:

TABLE 1

| Reactants | Broadest | Secondary |
|---|---|---|
| $(SiO_2 + GeO_2)/Al_2O_3$ | 30 to 600 | 60 to 500 |
| $Q/(SiO_2 + GeO_2)$ | 0.10 to 1.00 | 0.20 to 0.70 |
| $F/(SiO_2 + GeO_2)$ | 0.10 to 1.00 | 0.20 to 0.70 |
| $H_2O/(SiO_2 + GeO_2)$ | 2 to 10 | 4 to 8 | wherein Q comprises 3,3'-[2,6-naphthalenebis(methylene)]bis[1,2-dimethyl-1H-imidazolium] dications.

In some aspects, the reaction mixture can have a $SiO_2/GeO_2$ molar ratio in a range of from 4 to 12 (e.g., from 6 to 10).

The FAU framework type zeolite can be ammonium-form zeolites or hydrogen-form zeolites (e.g., $NH_4$-form zeolite Y, H-form zeolite Y). Examples of the FAU framework type zeolite include zeolite Y (e.g., CBV720, CBV760, CBV780, HSZ-385HUA, and HSZ-390HUA). Preferably, the FAU framework type zeolite is zeolite Y. More preferably, zeolite Y has a $SiO_2/Al_2O_3$ molar ratio in a range of about 30 to about 500. The FAU framework type zeolite can comprise two or more zeolites. Typically, the two or more zeolites are Y zeolites having different $SiO_2/Al_2O_3$ molar ratios. The FAU framework type zeolite can also be the only silica and aluminum source to form the aluminogermanosilicate molecular sieve.

Sources of germanium include germanium oxide and germanium alkoxides (e.g., germanium ethoxide).

Sources of fluoride ions include hydrogen fluoride, ammonium fluoride, and ammonium bifluoride.

SSZ-120 can be synthesized using a structure directing agent (Q) comprising 3,3'-[2,6-naphthalenebis(methylene)]bis[1,2-dimethyl-1H-imidazolium] dications, represented by the following structure (1):

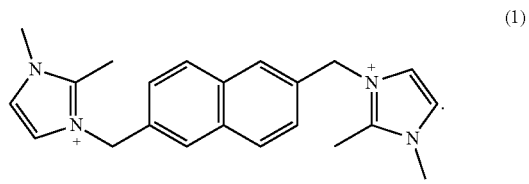

Suitable sources of Q are the hydroxides, chlorides, bromides, and/or other salts of the diquaternary ammonium compound.

The reaction mixture can contain seeds of a molecular sieve material, such as SSZ-120 from a previous synthesis, in an amount of from 0.01 to 10,000 ppm by weight (e.g., 100 to 5000 ppm by weight) of the reaction mixture. Seeding can be advantageous to improve selectivity for SSZ-120 and/or to shorten the crystallization process.

It is noted that the reaction mixture components can be supplied by more than one source. Also, two or more reaction components can be provided by one source. The reaction mixture can be prepared either batchwise or continuously.

Crystallization and Post-Synthesis Treatment

Crystallization of the molecular sieve from the above reaction mixture can be carried out under either static, tumbled or stirred conditions in a suitable reactor vessel, such as polypropylene jars or Teflon-lined or stainless-steel autoclaves placed in convection oven maintained at a temperature of from 100° C. to 200° C. for a time sufficient for crystallization to occur at the temperature used (e.g., 1 day to 14 days). The hydrothermal crystallization process is usually conducted under autogenous pressure.

Once the desired molecular sieve crystals have formed, the solid product is separated from the reaction mixture by standard separation techniques such as filtration or centrifugation. The recovered crystals are water-washed and then dried, for several seconds to a few minutes (e.g., from 5 seconds to 10 minutes for flash drying) or several hours (e.g., from 4 to 24 hours for oven drying at 75° C. to 150° C.), to obtain as-synthesized SSZ-120 crystals having at least a portion of the structure directing agent within its pores. The drying step can be performed at atmospheric pressure or under vacuum.

The as-synthesized molecular sieve may be subjected to thermal treatment, ozone treatment, or other treatment to remove part or all of the structure directing agent used in its synthesis. Removal of the structure directing agent may be carried out by thermal treatment (i.e., calcination) in which the as-synthesized molecular sieve is heated in air or inert gas at a temperature sufficient to remove part or all of the structure directing agent. While sub-atmospheric pressure may be used for the thermal treatment, atmospheric pressure is desired for reasons of convenience. The thermal treatment may be performed at a temperature at least 370° C. for at least a minute and generally not longer than 20 hours (e.g., from 1 to 12 hours). The thermal treatment can be performed at a temperature of up to 925° C. For example, the thermal treatment may be conducted at a temperature of from 400° C. to 600° C. in air for approximately 1 to 8 hours. The thermally-treated product, especially in its metal, hydrogen and ammonium forms, is particularly useful in the catalysis of certain organic (e.g., hydrocarbon) conversion reactions.

Any extra-framework metal cations in the molecular sieve can be replaced in accordance with techniques well known in the art (e.g., by ion exchange) with hydrogen, ammonium, or any desired metal cation.

Characterization of the Molecular Sieve

In its as-synthesized and anhydrous form, molecular sieve SSZ-120 can have a chemical composition comprising the following molar relationship set forth in Table 2:

TABLE 2

|  | Broadest | Secondary |
|---|---|---|
| $(SiO_2 + GeO_2)/Al_2O_3$ | ≥30 | ≥60 |
| $Q/(SiO_2 + GeO_2)$ | >0 to 0.1 | >0 to 0.1 | wherein Q comprises 3,3'-[2,6-naphthalenebis(methylene)]bis[1,2-dimethyl-1H-imidazolium] dications.

In some aspects, the molecular sieve can have a $SiO_2/GeO_2$ molar ratio in a range of from 4 to 12 (e.g., 6 to 10).

In its calcined form, molecular sieve SSZ-120 can have a chemical composition comprising the following molar relationship:

$$Al_2O_3 : (n)(SiO_2+GeO_2)$$

wherein n is ≥30 (e.g., 30 to 600, 60, 60 to 500, or 100 to 300).

Molecular sieve SSZ-120 has a powder X-ray diffraction pattern which, in its as-synthesized form, includes at least the peaks set forth in Table 3 below and which, in its calcined form, includes at least the peaks set forth in Table 4.

TABLE 3

Characteristic Peaks for As-Synthesized SSZ-120

| 2-Theta [°] | d-Spacing [nm] | Relative Intensity [100 × I/Io] |
|---|---|---|
| 6.8 | 1.31 | W |
| 9.4 | 0.94 | W |
| 15.7 | 0.57 | M |
| 21.0 | 0.42 | M |
| 22.0 | 0.40 | VS |
| 25.9 | 0.34 | M |
| 26.9 | 0.33 | M |

TABLE 4

Characteristic Peaks for Calcined SSZ-120

| 2-Theta [°] | d-Spacing [nm] | Relative Intensity [100 × I/Io] |
|---|---|---|
| 6.8 | 1.30 | W |
| 9.5 | 0.93 | W |
| 15.6 | 0.57 | M |
| 21.0 | 0.42 | W |
| 22.2 | 0.40 | VS |
| 25.9 | 0.34 | M |
| 26.9 | 0.33 | M |

The powder X-ray diffraction patterns presented herein were collected by standard techniques using copper K-alpha radiation. As will be understood by those of skill in the art, the determination of the parameter 2-theta is subject to both human and mechanical error, which in combination can impose an uncertainty of about ±0.3° on each reported value of 2-theta. This uncertainty is, of course, also manifested in the reported values of the d-spacings, which are calculated from the 2-theta values using Bragg's law. The relative intensities of the lines, I/Io, represents the ratio of the peak intensity to the intensity of the strongest line, above background. The intensities are uncorrected for Lorentz and polarization effects. The relative intensities are given in terms of the symbols VS=very strong (>60 to 100), S=strong (>40 to 60), M=medium (>20 to 40), and W=weak (>0 to 20).

Minor variations in the powder X-ray diffraction pattern (e.g., experimental variation in peak ratios and peak positions) can result from variations in the atomic ratios of the framework atoms due to changes in lattice constants. In addition, sufficiently small crystals may affect the shape and intensity of peaks, possibly leading to peak broadening. Calcination can also cause minor shifts in the powder X-ray diffraction pattern compared to the pre-calcination powder X-ray diffraction pattern. Notwithstanding these minor perturbations, the crystal lattice structure may remain unchanged following calcination.

The syntheses described herein can produce a molecular sieve having a small crystal size, such that the total surface area of the material can be at least 500 $m^2/g$ and the external surface area can be at least 100 $m^2/g$. In some aspects, the molecular sieve described herein can comprise crystals having a total external surface area of at least 600 $m^2/g$, at least 625 $m^2/g$, at least or at least 650 $m^2/g$, such as from 500 to 800 $m^2/g$, from 600 to 800 $m^2/g$, or from 650 to 800 $m^2/g$. Additionally or alternatively, the molecular sieve described herein can comprise crystals having an external surface area of at least 100 $m^2/g$, at least 110 $m^2/g$, at least 120 $m^2/g$, at least 130 $m^2/g$, or at least 140 $m^2/g$, such as from 100 to 300 $m^2/g$, from 120 to 300 $m^2/g$, or from 140 to 300 $m^2/g$. All surface area values given herein are determined from nitrogen physisorption using the t-plot method. Details of this method are described by B. C. Lippens and J. H. de Boer (J. Catal. 1965, 4, 319-323).

INDUSTRIAL APPLICABILITY

Molecular sieve SSZ-120 (where part or all of the structure directing agent is removed) may be used as a sorbent or as a catalyst to catalyze a wide variety of organic compound conversion processes including many of present commercial/industrial importance. Examples of chemical conversion processes which are effectively catalyzed by SSZ-120, by itself or in combination with one or more other catalytically active substances including other crystalline catalysts, include those requiring a catalyst with acid activity. Examples of organic conversion processes which may be catalyzed by SSZ-120 include aromatization, cracking, hydrocracking, disproportionation, alkylation, oligomerization, and isomerization.

As in the case of many catalysts, it may be desirable to incorporate SSZ-120 with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring, or in the form of gelatinous precipitates or gels, including mixtures of silica and metal oxides. Use of a material in conjunction with SSZ-120 (i.e., combined therewith or present during synthesis of the new material) which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays (e.g., bentonite and kaolin) to improve the crush strength of the catalyst under commercial operating conditions. These materials (i.e., clays, oxides, etc.) function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with SSZ-120 include the montmorillonite and kaolin family, which families include the sub-bentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with SSZ-120 also include inorganic oxides, such as silica, zirconia, titania, magnesia, beryllia, alumina, and mixtures thereof.

In addition to the foregoing materials, SSZ-120 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of SSZ-120 and inorganic oxide matrix may vary widely, with the SSZ-120 content ranging from 1 to 90 wt. % (e.g., 2 to 80 wt. %) of the composite.

EXAMPLES

The following illustrative examples are intended to be non-limiting.

Example 1

Synthesis of 3,3'-[2,6-naphthalenebis(methylene)]bis[1,2-dimethyl-1H-imidazolium] dihydroxide A 250 mL round bottom flask equipped with a magnetic stir bar was charged with 5 g of 2,6-bis(bromomethyl)naphthalene, 3.83 g of 1,2-dimethylimidazole and 100 mL of methanol. A reflux condenser was then attached, and the mixture heated at 65° C. for 3 days. After cooling, methanol was removed on a rotary evaporator to provide white solids. The initially recovered solids from rotary evaporation were further purified by recrystallization from cold ethanol. The recrystallized dibromide salt was pure by $^1$H- and $^{13}$C-NMR spectroscopy.

The dibromide salt was exchanged to the corresponding dihydroxide salt by stirring it with hydroxide exchange resin in deionized water overnight. The solution was filtered, and the filtrate was analyzed for hydroxide concentration by titration of a small sample with a standardized solution of 0.1 N HCl.

Example 2

Synthesis of SSZ-120

Into a tared 23 mL Parr reactor was added 0.27 g of Tosoh HSZ-390HUA Y-zeolite (SAR=500), 0.05 g of GeO$_2$ and 2.5 mmol of an aqueous 3,3'-[2,6-naphthalenebis(methylene)]bis[1,2-dimethyl-1H-imidazolium] dihydroxide solution. The reactor was then placed in a vented hood and water was allowed to evaporate to bring the H$_2$O/(SiO$_2$+GeO$_2$) molar ratio to 7 (as determined by the total mass of the suspension). Then, 2.5 mmol of HF was added and the reactor was heated to 160° C. with tumbling at 43 rpm for about 7 days. The solid products were recovered by centrifugation, washed with deionized water and dried at 95° C.

Powder XRD of the as-synthesized product gave the pattern indicated in FIG. 1 and showed the product to be a pure form of a new phase, SSZ-120. Significantly decreased crystal size is inferred from the peak broadening in the powder XRD pattern.

FIGS. 2(A)-2(D) show illustrative SEM images of the as-synthesized product at various magnifications.

The product had a SiO$_2$/GeO$_2$ molar ratio of 8, as determined by Inductively Coupled Plasma—Atomic Emission Spectroscopy (ICP-AES).

Example 3

Calcination of SSZ-120

The as-synthesized molecular sieve of Example 1 was calcined inside a muffle furnace under a flow of air heated to 550° C. at a rate of 1° C./minute and held at 550° C. for 5 hours, cooled and then analyzed by powder XRD.

Figure 3:
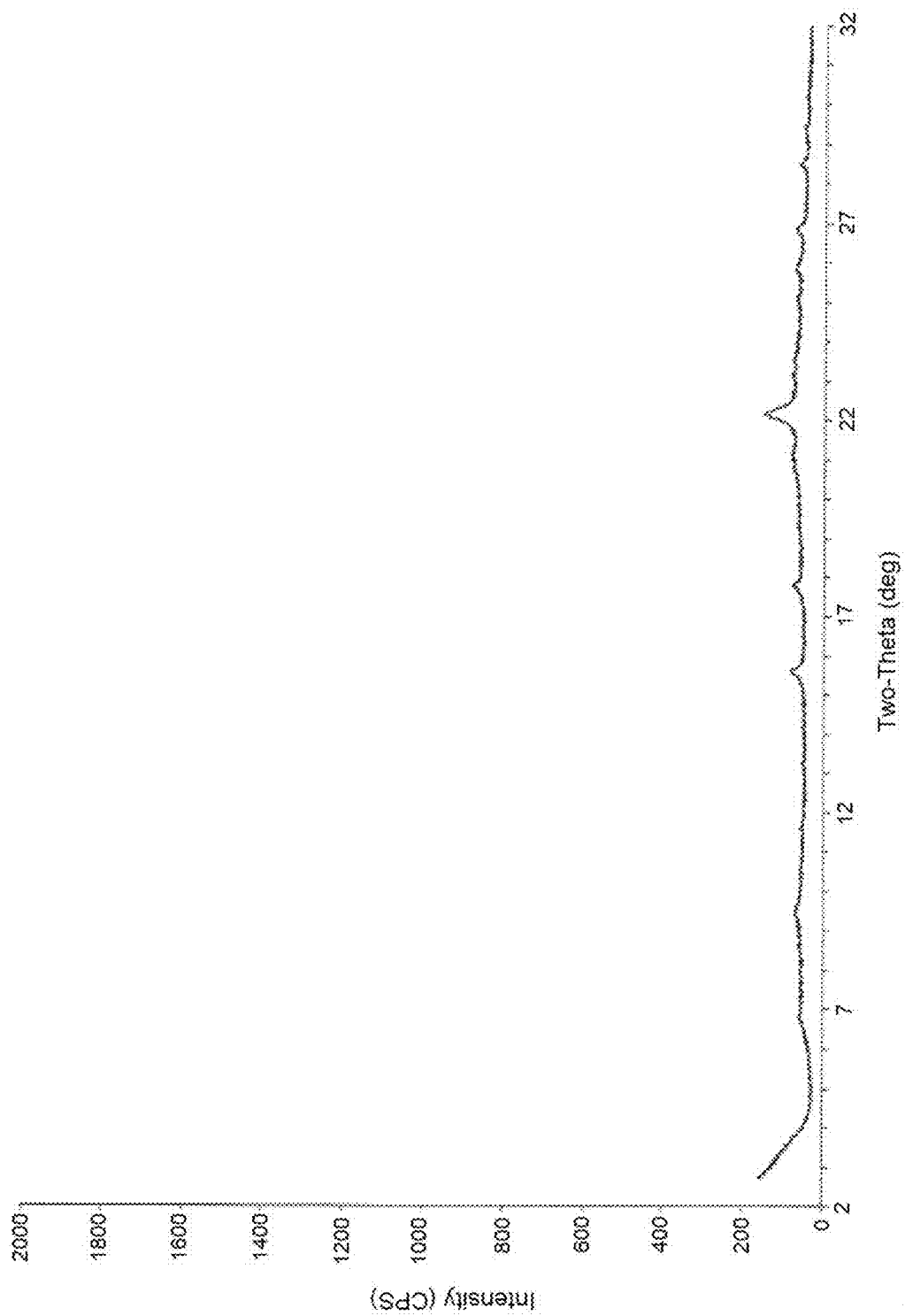
FIG. 3 shows the powder XRD pattern of the calcined product of Example 3.

The powder XRD pattern of the calcined material is shown in FIG. 3 and indicates that the material remains stable after calcination to remove the structure directing agent.

Example 4

Example 2 was repeated using Zeolyst CBV780 Y-zeolite (SAR=80) as the FAU source. Powder XRD showed the product to be SSZ-120.

Example 5

Example 2 was repeated using Zeolyst CBV760 Y-zeolite (SAR=60) as the FAU source. Powder XRD showed the product to be SSZ-120.

The product was calcined as described in Example 2. The surface area of the sample was then measured using nitrogen physisorption and the data were analyzed with the t-plot method. The determined total surface area was 693 m$^2$/g and the external surface area was 144 m$^2$/g. The micropore volume was 0.2666 cm$^3$/g.

Example 6

Example 2 was repeated using Zeolyst CBV720 Y-zeolite (SAR=30) as the FAU source. Powder XRD showed the product to be SSZ-120.

Example 7

Brønsted Acidity

Brønsted acidity of the molecular sieve of Example 5 in its calcined form was determined by n-propylamine temperature-programmed desorption (TPD) adapted from the published descriptions by T. J. Gricus Kofke et al. (*J. Catal.* 1988, 114, 34-45); T. J. Gricus Kofke et al. (*J. Catal.* 1989, 115, 265-272); and J. G. Tittensor et al. (*J. Catal.* 1992, 138, 714-720). A sample was pre-treated at 400° C.-500° C. for 1 hour in flowing dry H$_2$. The dehydrated sample was then cooled down to 120° C. in flowing dry helium and held at 120° C. for 30 minutes in a flowing helium saturated with n-propylamine for adsorption. The n-propylamine-saturated sample was then heated up to 500° C. at a rate of 10° C./minute in flowing dry helium. The Brønsted acidity was calculated based on the weight loss vs. temperature by thermogravimetric analysis (TGA) and effluent $NH_3$ and propene by mass spectrometry. The sample had a Brønsted acidity of 250 μmol/g, indicating that aluminum sites are incorporated into the framework of the molecular sieve.

Example 8

Constraint Index Testing

Constraint Index is a test to determine shape-selective catalytic behavior in molecular sieves. It compares the reaction rates for the cracking of n-hexane (n-C6) and its isomer 3-methylpentane (3-MP) under competitive conditions (see V. J. Frillette et al., *J. Catal.* 1981, 67, 218-222).

The hydrogen form of the molecular sieve prepared per Example 5 was pelletized at 4 kpsi, crushed and granulated to 20-40 mesh. A 0.6 g sample of the granulated material was calcined in air at 540° C. for 4 hours and cooled in a desiccator to ensure dryness. Then, 0.47 g of material was packed into a ¼ inch stainless steel tube with alundum on both sides of the molecular sieve bed. A furnace (Applied Test Systems, Inc.) was used to heat the reactor tube. Nitrogen was introduced into the reactor tube at 9.4 mL/minute and at atmospheric pressure. The reactor was heated to about 700° F. (371° C.), and a 50/50 feed of n-hexane and 3-methylpentane was introduced into the reactor at a rate of 8 μL/minute. The feed was delivered by an ISCO pump. Direct sampling into a GC began after 15 minutes of feed introduction. Test data results after 15 minutes on stream (700° F.) are presented in Table 5.

TABLE 5

| Constraint Index Test | |
|---|---|
| n-Hexane Conversion, % | 64.8 |
| 3-Methylpentane Conversion, % | 93.3 |
| Feed Conversion, % | 79.1 |
| Constraint Index (excluding 2MP) | 0.39 |
| Constraint Index (including 2MP) | 0.39 |

Example 9

Hydroconversion of n-Decane

Material from Example 5 was calcined in air at 595° C. for 5 hours. After calcination, the material was loaded with palladium by mixing for three days at room temperature 4.5 g of a 0.148 N $NH_4OH$ solution with 5.5 g of deionized water and then a $(NH_3)_4Pd(NO_3)_2$ solution (buffered at pH 9.5) such that 1 g of this solution mixed in with 1 g of molecular sieve provided a 0.5 wt. % Pd loading. The recovered Pd/SSZ-120 material was washed with deionized water, dried at 95° C., and then calcined to 300° C. for 3 hours. The calcined Pd/SSZ-120 catalyst was then pelletized, crushed, and sieved to 20-40 mesh.

Figure 4:
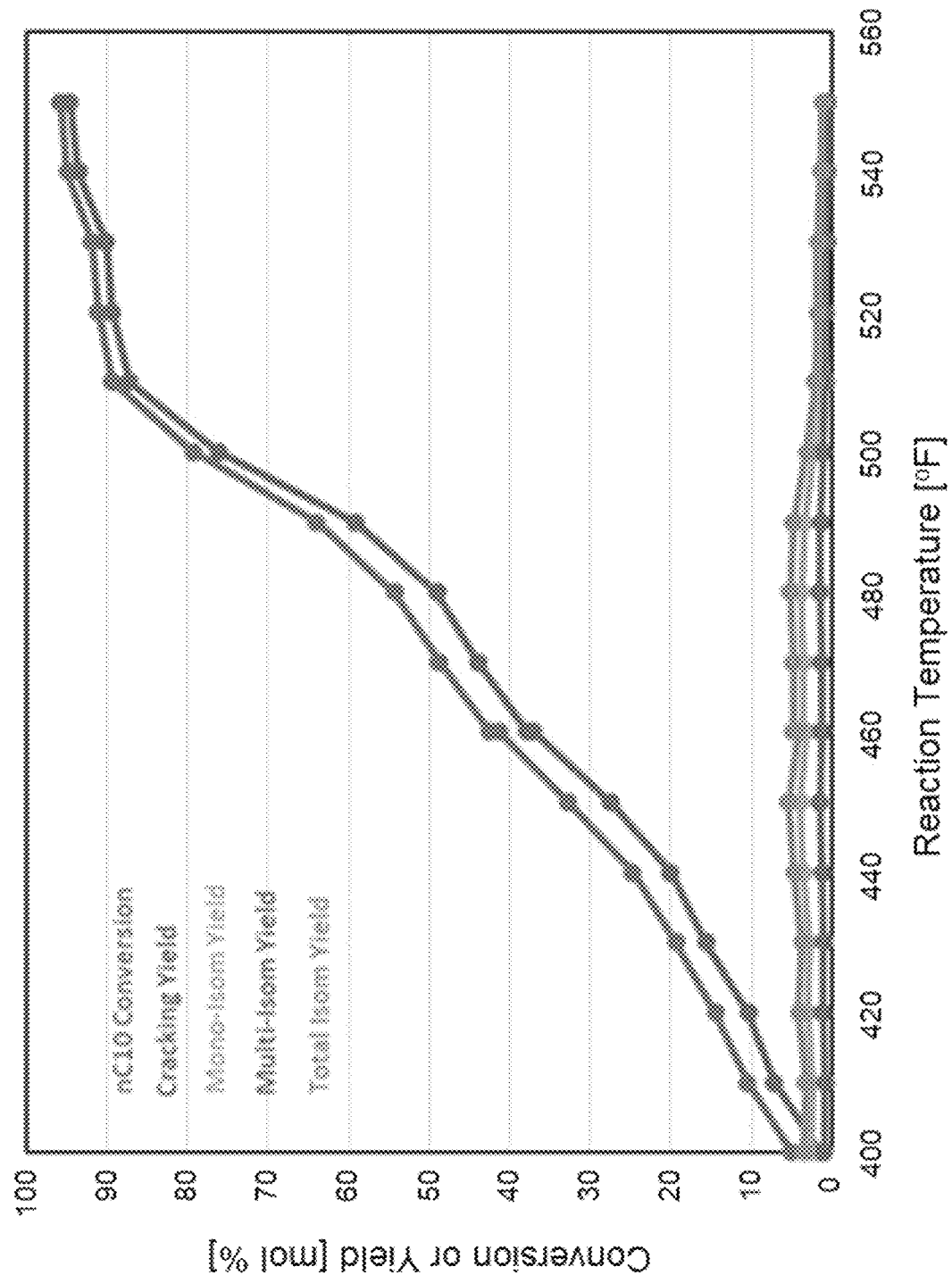
FIG. 4 is a graph illustrating the relationship between conversion or yield and temperature in the hydroconversion of n-decane over a Pd/SSZ-120 catalyst.

0.5 g of the Pd/SSZ-120 catalyst was loaded in the center of a 23 inch-long×¼ inch outside diameter stainless steel reactor tube with alundum loaded upstream of the catalyst for preheating the feed (a total pressure of 1200 psig; a down-flow hydrogen rate of 160 mL/minute when measured at 1 atmosphere pressure and 25° C.; and a down-flow liquid feed rate of 1 mL/hour). All materials were first reduced in flowing hydrogen at about 315° C. for 1 hour. Products were analyzed by on-line capillary GC once every 60 minutes. Raw data from the GC was collected by an automated data collection/processing system and hydrocarbon conversions were calculated from the raw data. Conversion is defined as the amount n-decane reacted to produce other products (including iso-C10). Yields are expressed as mole percent of products other than n-decane and include iso-C10 isomers as a yield product. The results are shown in FIG. 4 and indicate that the catalyst is quite active and not particularly selective for isomerization, making considerable cracked product from n-decane.

The invention claimed is:

1. An aluminogermanosilicate molecular sieve having, in its calcined form, a powder X-ray diffraction pattern including the peaks in the following table:

| 2-Theta [°] | d-Spacing [nm] | Relative Intensity [100 × I/Io] |
|---|---|---|
| 6.8 | 1.30 | W |
| 9.5 | 0.93 | W |
| 15.6 | 0.57 | M |
| 21.0 | 0.42 | W |
| 22.2 | 0.40 | VS |
| 25.9 | 0.34 | M |
| 26.9 | 0.33 | M. |

2. The aluminogemanosilicate molecular sieve of claim 1, the molecular sieve comprising crystals having a total surface area of at least 500 m²/g, as determined by the t-plot method for nitrogen physisorption, and/or an external surface area in a range of at least 100 m²/g, as determined by determined from the t-plot method of nitrogen physisorption.

3. The aluminogemanosilicate molecular sieve of claim 2, wherein the total surface area is in a range of from 500 to 800 m²/g.

4. The aluminogemanosilicate molecular sieve of claim 2, wherein the external surface area is in a range of from 100 to 300 m²/g.

5. The aluminogermanosilicate molecular sieve of claim 1, having a composition comprising the molar relationship:

$$Al_2O_3: (n)(SiO_2+GeO_2)$$

wherein n is ≥30.

6. An aluminogermanosilicate molecular sieve having, in its as-synthesized form, a powder X-ray diffraction pattern including the peaks in the following table:

| 2-Theta [°] | d-Spacing [nm] | Relative Intensity [100 × I/Io] |
|---|---|---|
| 6.8 | 1.31 | W |
| 9.4 | 0.94 | W |
| 15.7 | 0.57 | M |
| 21.0 | 0.42 | M |
| 22.0 | 0.40 | VS |
| 25.9 | 0.34 | M |
| 26.9 | 0.33 | M. |

7. The aluminogermanosilicate molecular sieve of claim 6, having a composition, in terms of molar ratios, as follows:

| $(SiO_2 + GeO_2)/Al_2O_3$ | ≥30 |
|---|---|
| $Q/(SiO_2 + GeO_2)$ | >0 to 0.1 | wherein Q comprises 3,3'-[2,6-naphthalenebis(methylene)]bis[1,2-dimethyl-1H-imidazolium] dications.

8. The aluminogermanosilicate molecular sieve of claim 6, having a chemical composition comprising the following molar relationship:

| | |
|---|---|
| $(SiO_2 + GeO_2)/Al_2O_3$ | ≥60 |
| $Q/(SiO_2 + GeO_2)$ | >0 to 0.1 | wherein Q comprises 3,3'-[2,6-naphthalenebis(methylene)]bis[1,2-dimethyl-1H-imidazolium] dications.

9. A method of synthesizing an aluminogermanosilicate molecular sieve, the method comprising:
  (1) providing a reaction mixture comprising:
    (a) a FAU framework type zeolite;
    (b) a source of germanium;
    (c) a structure directing agent (Q) comprising 3,3'-[2,6-naphthalenebis(methylene)]bis[1,2-dimethyl-1H-imidazolium] dications;
    (d) a source of fluoride ions; and
    (e) water; and
  (2) subjecting the reaction mixture to crystallization conditions sufficient to form crystals of the aluminogermanosilicate molecular sieve.

10. The method of claim 9, wherein the reaction mixture has a composition, in terms of molar ratios, as follows:

| | |
|---|---|
| $(SiO_2 + GeO_2)/Al_2O_3$ | 30 to 600 |
| $Q/(SiO_2 + GeO_2)$ | 0.10 to 1.00 |
| $F/(SiO_2 + GeO_2)$ | 0.10 to 1.00 |
| $H_2O/(SiO_2 + GeO_2)$ | 2 to 10. |

11. The method of claim 9, wherein the reaction mixture has a composition, in terms of molar ratios, as follows:

| | |
|---|---|
| $(SiO_2 + GeO_2)/Al_2O_3$ | 60 to 500 |
| $Q/(SiO_2 + GeO_2)$ | 0.20 to 0.70 |
| $F/(SiO_2 + GeO_2)$ | 0.20 to 0.70 |
| $H_2O/(SiO_2 + GeO_2)$ | 4 to 8. |

12. The method of claim 9, wherein the FAU framework type zeolite is zeolite Y.

13. The method of claim 9, wherein the crystallization conditions include heating the reaction mixture under autogenous pressure at a temperature of from 100° C. to 200° C. and for a time of from 1 day to 14 days.

14. A process for converting a feedstock comprising an organic compound to a conversion product, the process comprising contacting the feedstock at organic compound conversion conditions with a catalyst comprising the aluminogermanosilicate molecular sieve of claim 1.

\* \* \* \* \*